United States Patent [19]

Rettig et al.

[11] Patent Number: 5,059,523
[45] Date of Patent: Oct. 22, 1991

[54] CELL-SURFACE GLYCOPROTEINS OF HUMAN SARCOMAS

[75] Inventors: Wolfgang J. Rettig; Pilar Garin-Chesa, both of New York; H. Richard Beresford, Century Island, all of N.Y.; Herbert F. Oettgen, New Canaan, Conn.; Myron R. Melamed, Dobbs Ferry; Lloyd J. Old, New York, both of N.Y.

[73] Assignee: Sloan-Kettering Institute for Cancer Research, New York, N.Y.

[21] Appl. No.: 189,238

[22] Filed: May 2, 1988

[51] Int. Cl.$^5$ .................. G01N 33/53; G01N 33/567; C12N 15/00; C07K 15/14
[52] U.S. Cl. .................. 435/7.23; 435/172.2; 435/240.77; 435/960; 436/64; 436/503; 436/548; 436/813; 530/387; 530/809; 935/95; 935/103; 935/106; 935/110
[58] Field of Search .................. 435/7, 172.2, 240.27, 435/7.1, 7.23, 7.9, 960; 436/501, 548, 813, 503, 64; 424/85; 530/387, 809; 935/107, 110, 95, 103, 106

[56] References Cited

U.S. PATENT DOCUMENTS 4,643,971 2/1987 Fradet et al. .................. 436/548
4,725,538 2/1988 Senger .................. 435/7

OTHER PUBLICATIONS

Rettig et al, Cancer Research, vol. 47, Mar. 1, 1987, pp. 1383–1389.
Gorden et al, Cell, vol. 50, Jul. 31, 1987, pp. 445–452.
Rettig et al, Exp. Med., vol. 164, Nov. 1986, pp. 1581–1599.
Iwasaki et al, Am. J. of Path., vol. 128, No. 3, Sep. 1987, pp. 528–537.
Sato et al, Am. J. of Path., vol. 125, 1986, pp. 431–435.
Rettig et al, Biological Abstract, vol. 83(1), 1987, Abstract No. 3677 (Somatic Cell Mol Genet, 12(5): 441–448, 1986).
Rettig et al, Cancer Research, vol. 46, Dec. 1986, pp. 6406–6412.
Rettig et al, The Journal of Immunology, vol. 138 (12), Jun. 15, 1987, pp. 4484–4489.
Thomson et al, Experimental Cell Research, vol. 174(2), Feb. 1988, pp. 533–539.
Azumi et al, A.S.C.P., vol. 88(3), Sep. 1987, pp. 286–296.

Primary Examiner—Esther L. Kepplinger
Assistant Examiner—Florina B. Hoffer
Attorney, Agent, or Firm—John P. White

[57] ABSTRACT

This invention provides a method of identifying mesenchymal tissues as normal, proliferatively active or malignant. This invention also provides a method of distinguishing subsets of sarcomas with distinctive antigenic phenotypes. This invention also provides a method of diagnosing mesenchymal tumors. Finally, this invention provides a monoclonal antibody designated G171 and the hybridoma cell line producing said monoclonal antibody (ATCC No. HB9254).

7 Claims, 10 Drawing Sheets

A B C D E F G H I J K L M

CELL-SURFACE GLYCOPROTEINS OF HUMAN SARCOMAS

This invention was made with government support under Grant Numbers CA-08748 and CA-25803 from the National Cancer Institute The U.S. Government has certain rights in the invention.

BACKGROUND OF THE INVENTION

Throughout this application, various publications are referenced by arabic numerals within parentheses. Full citations for these publications may be found at the end of the specification immediately preceding the claims The disclosures of these publications in their entireties are hereby incorporated by reference into this application in order to more fully describe the state of the art as known to those skilled therein as of the date of the invention described and claimed.

Distinct pathways and stages of cellular differentiation are associated with specific patterns of cell-surface antigen expression. This principle was first established through analysis of normal and malignant cells of hematopoietic origin and has been extended to the neuroectodermal lineage (1–7). The identification of an ordered progression of surface phenotypic changes during normal differentiation has permitted classification of leukemias and lymphomas, melanomas, astrocytomas, and neuroblastomas into subsets that show antigenic similarity to normal cells at distinct stages of hematopoietic or neuroectodermal differentiation (2–4, 6, 7). In contrast to the hematopoietic and neuroectodermal systems, little is known about surface antigenic phenotypes of mesenchymal cells and changes in antigen expression that accompany normal differentiation or malignant transformation of these cells. The present study describes six cell-surface glycoproteins that are differentially expressed during normal development, proliferative activation, or malignant transformation of mesenchymal cells and tissues.

SUMMARY OF THE INVENTION

This invention provides a method of identifying mesenchymal tissues as normal, proliferatively active or malignant which comprises contacting a mesechymal tissue sample with at least one monoclonal antibody selected from the group consisting of monoclonal antibodies F19, F24, G171, S5, G253 and K117 and observing reactions between said mesenchymal tissue sample and said antibody.

This invention also provides the aforementioned method wherein the mesenchymal tissue sample is human adult tissue or human fetal tissue.

This invention also provides a method of distinguishing subsets of sarcomas with distinctive antigenic phenotypes which comprises contacting a sarcoma tissue sample with at least one monoclonal antibody selected from the group consisting of monoclonal antibodies F19, G171, S5 and K117 and observing reactions between said sarcoma tissue sample and said antibody.

This invention further provides a method of diagnosing mesenchymal tumors which comprises contacting a mesenchymal tissue sample with at least one monoclonal antibody selected from the group consisting of monoclonal antibodies F19, G171 and S5 and observing reactions between said mesenchymal tissue sample and said antibody.

This invention also provides a hybridoma cell line producing the monoclonal antibody G171.

Finally, this invention provides the monoclonal antibody G171.

DETAILED DESCRIPTION OF THE INVENTION

Figure 1:
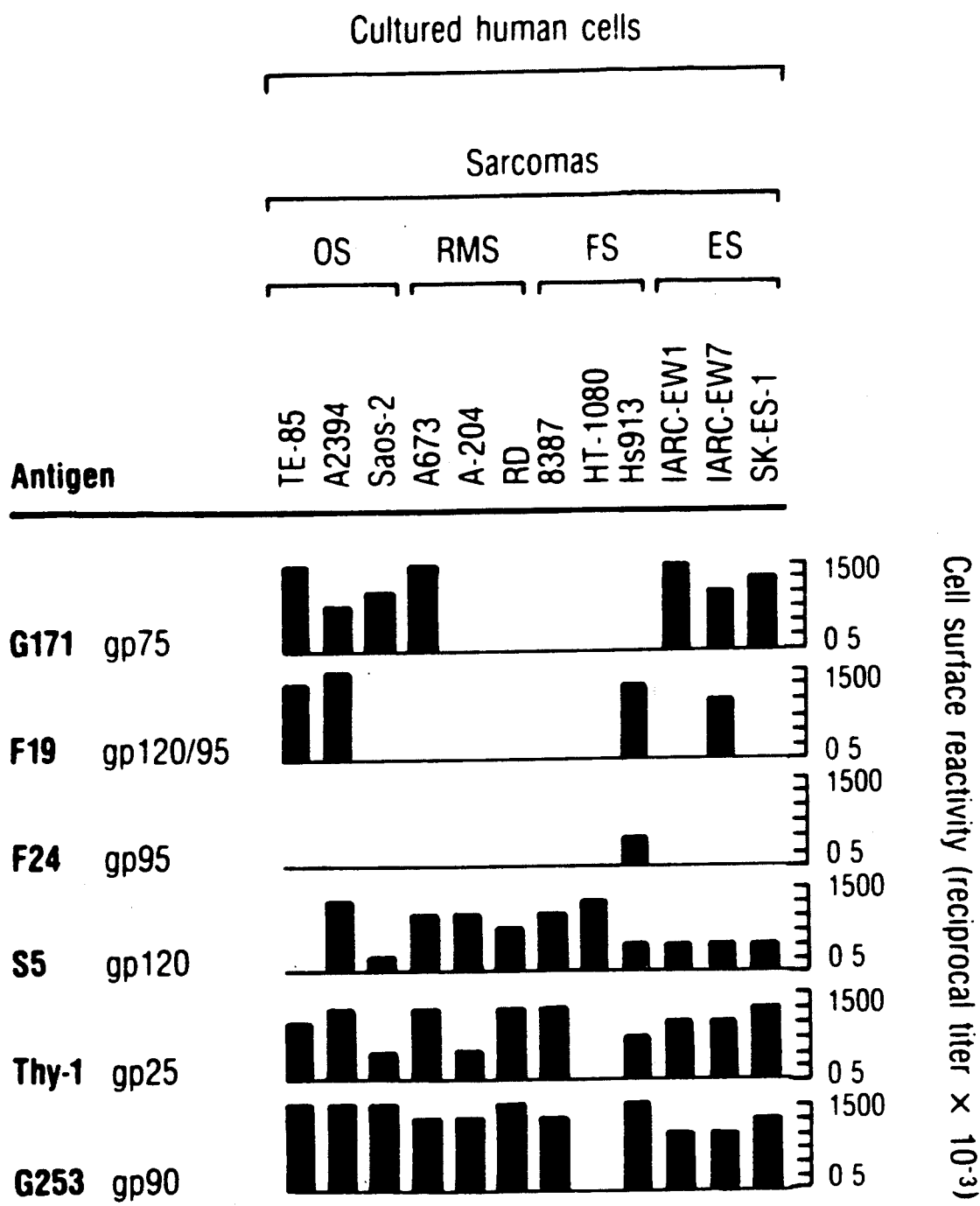
FIG. 1. Cell-surface phenotypes of established tumor cell lines and short-term cultures of normal fibroblasts. Results of mixed hemadsorption rosetting assay titration experiments (reciprocal titration end points) are shown in histograms, mAb dilutions tested (ascites fluid) are indicated on the right: 1:500, 1:2400, 1:12,000, 1:60,000, 1:300,00, and 1:1,500.000. Cell line origin is indicated as follows: OS, osteogenic sarcoma; RMS, rhabdomyosarcoma; FS, fibrosarcoma; ES, Ewing sarcoma; SV40-W138, SV40-transformed fetal lung fibroblasts; Nb, neuroblastoma; Rb, retinoblastoma; Ast, astrocytoma; and Mel, melanoma. For fibroblasts, number of cultures derived from various individuals are given in brackets. Typing results with mAbs F19, F24, S5, G253, and K117 on additional cell lines have been reported (7,9); analysis of an expanded cell line panel (8) with mAb G171 identified gp75 expression of 1 of 6 ovarian cancers (A10), 2 of 8 lung cancers (SK-LC-8 and -17), 1 of 12 astrocytomas (SK-GS-2), and a medulloblastoma (TE-671). All 10 renal, 5 breast, 8 bladder, and 8 colon cancers, 14 melanomas, and 20 leukemias tested were G171-, as were short-term cultures of normal kidney epithelial cells, keratinocytes, and skin melanocytes.
Figure 1:
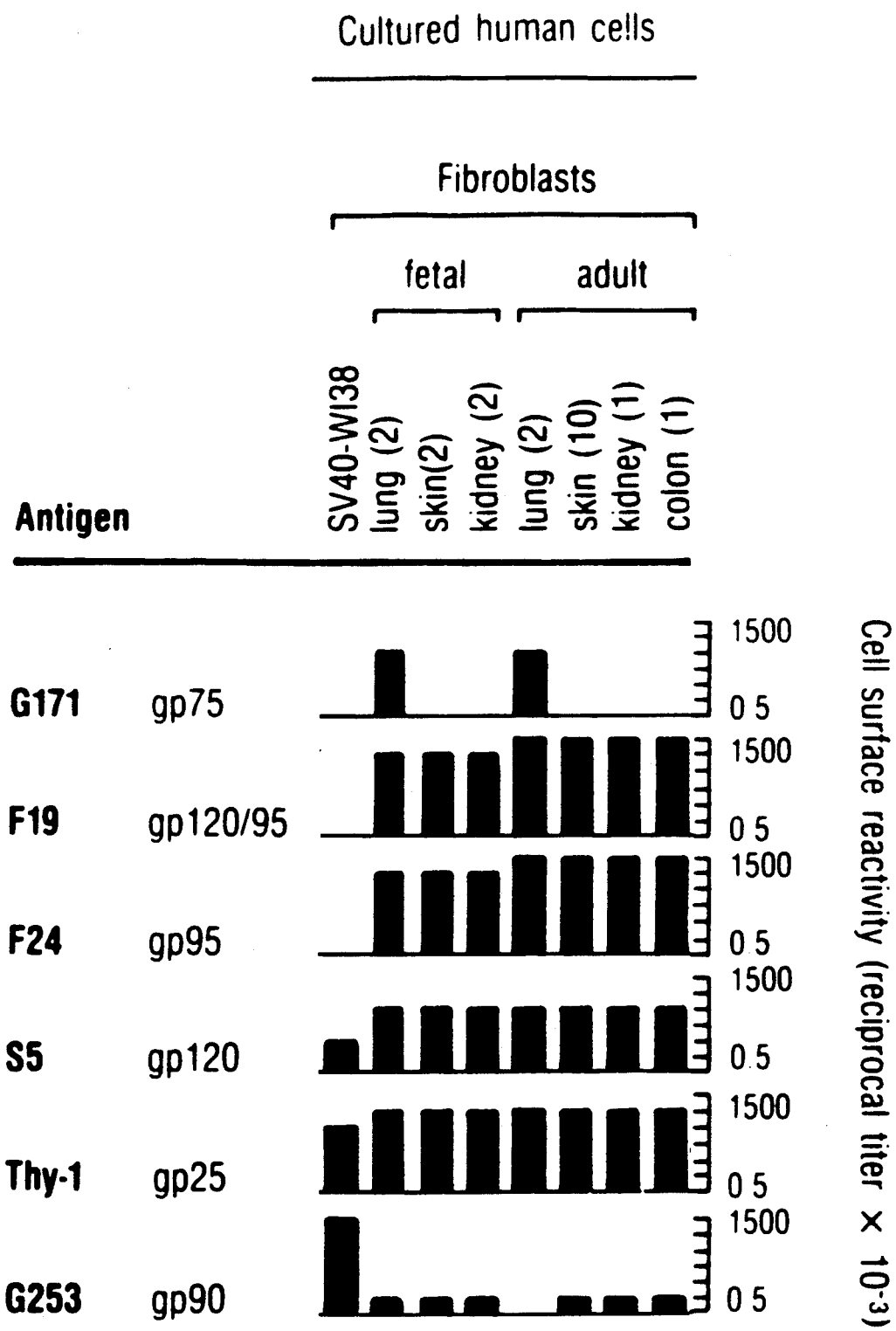
Figure 1:
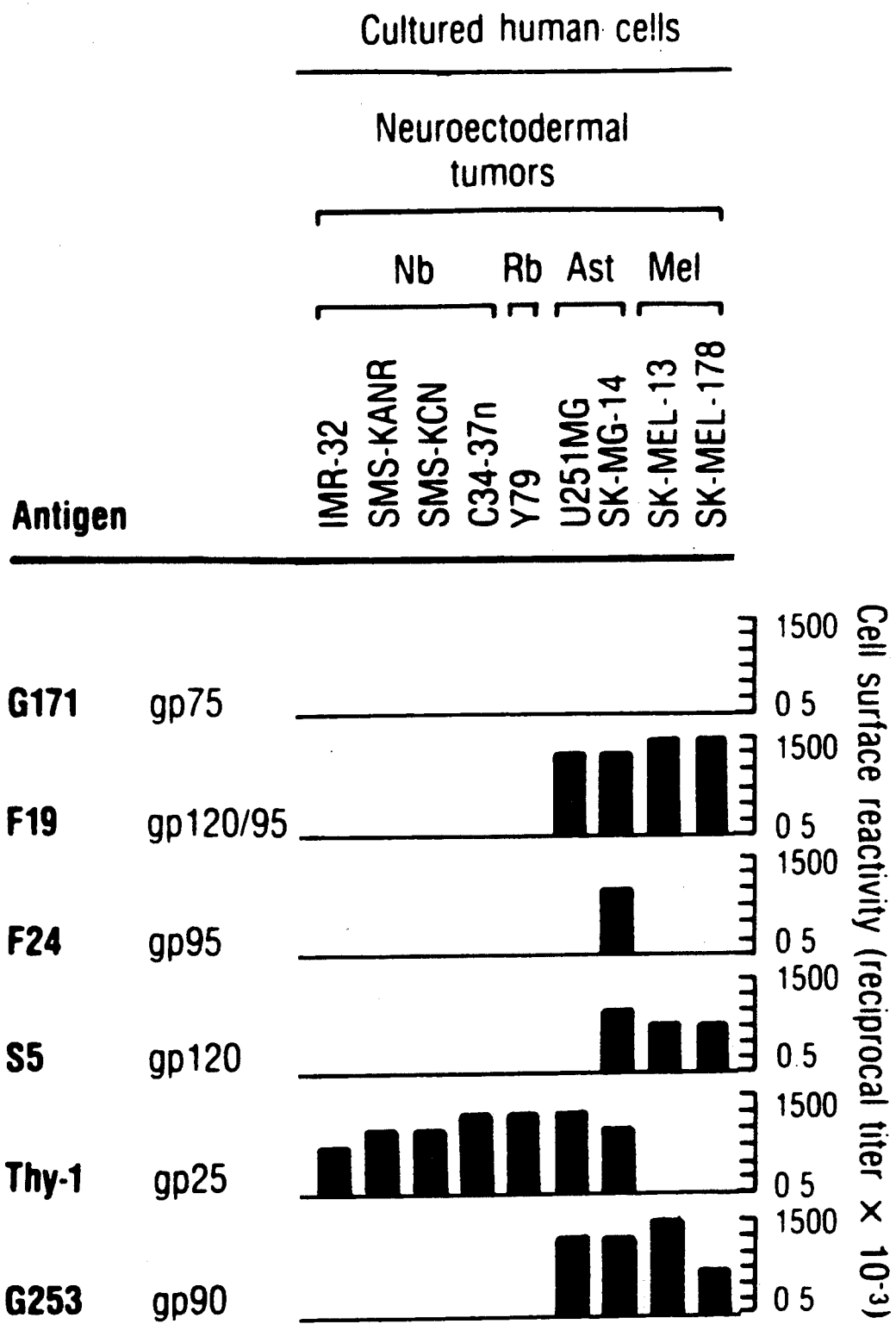
Figure 1:
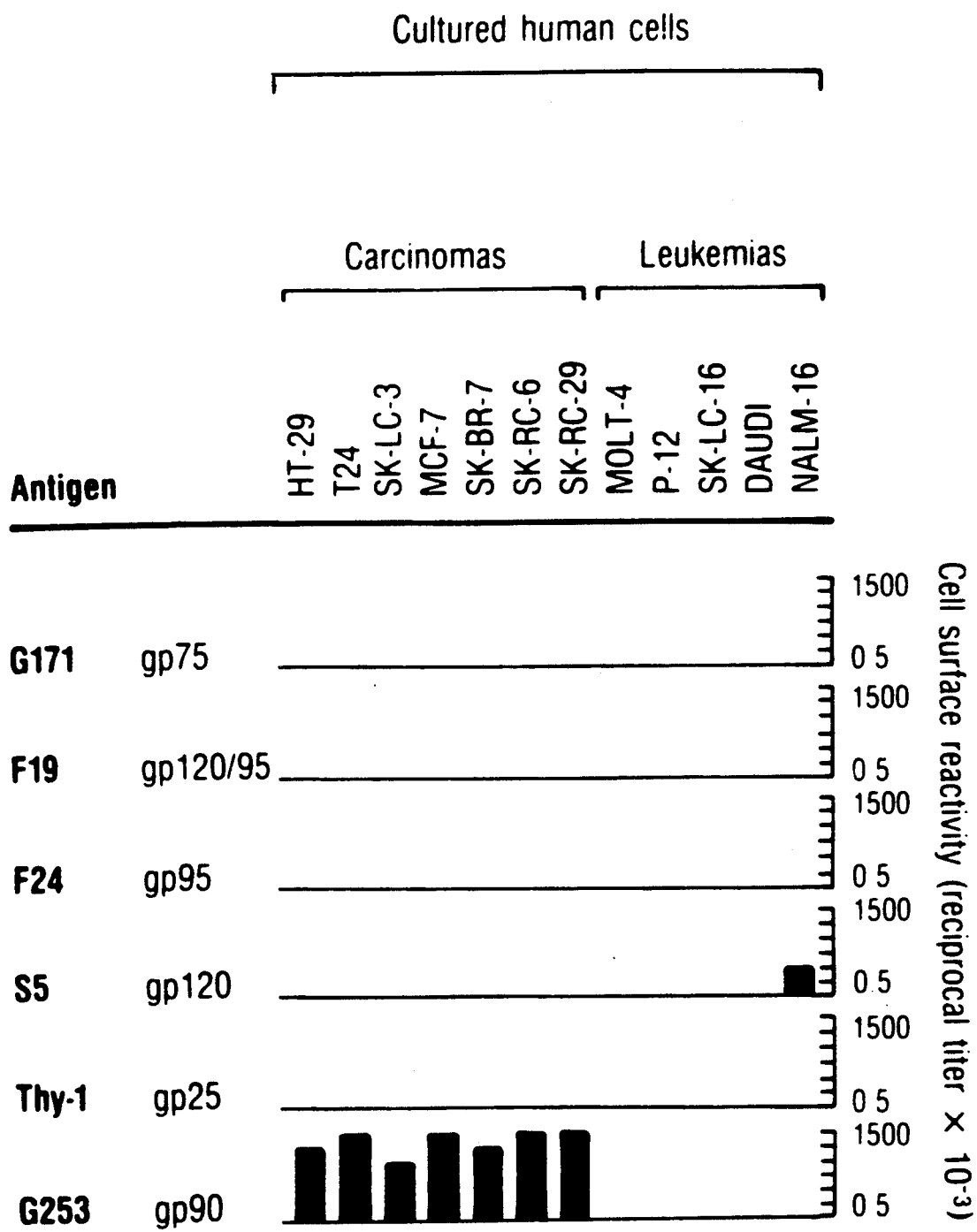

Hybridoma cell lines producing the monoclonal antibodies of the present invention have been deposited prior to filing of the present application at the American Type Culture Collection (ATCC), Bethesda, Md. and will be made available to the public during pendancy of any patent issuing therefrom in accordance with the Budapest Treaty. The hybridoma cell lines correspond to the monoclonal antibodies and bear ATCC accession numbers as follows:

| Monoclonal antibody | ATCC No. for related hybridoma | Date of Deposit |
| --- | --- | --- |
| F19 | HB8269 | 3/11/83 |
| F24 | HB9257 | 10/29/86 |
| G171 | HB9254 | 10/29/86 |
| S5 | HB9255 | 10/29/86 |
| G253 | HB9706 | 4/29/88 |
| K117 | HB8553 | 4/26/84 |

This invention provides a method of identifying mesenchymal tissues as normal, proliferatively active or malignant which comprises contacting a mesechymal tissue sample with at least one monoclonal antibody selected from the group consisting of monoclonal antibodies F1,, F24, G171, S5, G253 and K117 and observing reactions between said mesenchymal tissue sample and said antibody.

This invention also provides the aforementioned method wherein the mesenchymal tissue sample is human adult tissue or human fetal tissue.

This invention also provides a method of distinguishing subsets of sarcomas with distinctive antigenic phenotypes which comprises contacting a sarcoma tissue sample with at least one monoclonal antibody selected from the group consisting of monoclonal antibodies F19, G171, S5 and K117 and observing reactions between said sarcoma tissue sample and said antibody.

This invention further provides a method of diagnosing mesenchymal tumors which comprises contacting a mesenchymal tissue sample with at least one monoclonal antibody selected from the group consisting of monoclonal antibodies F19, G171 and S5 and observing reactions between said mesenchymal tissue sample and said antibody.

This invention also provides a hybridoma cell line producing the monoclonal antibody G171.

Finally, this invention provides the monoclonal antibody G171.

Materials and Methods

Cell Lines. Cell lines Hs 913T, TE-85, HT-1080, Saos-2, A-204, A673, RD, SK-ES-1, and WI-38 VA13 subline 2RA, were obtained from the American Type Culture Collection. Additional cell lines and normal cell cultures (4,8) were from the cell bank at SloanKettering Institute.

Antibodies and Serological Procedures. Monoclonal antibody G171 (IgG2a) was derived from a mouse immunized with human SK-GS-1 tumor cells as described (7). Monoclonal antibodies F19, F24, G253, S5, and K117 have been described (7, 9, 10). Mixed hemadsorption rosetting assays for detection of antigens on cultured cells were carried out as described (10).

Immunohistochemical Procedures. Tissues were obtained at autopsy or from surgical specimens and quick-frozen as described (11) or, for some experiments with monoclonal antibody K117, paraffin-embedded by the AMeX method (12); 5 μm-sections were cut, mounted on gelatin-coated slides, air-dried, and fixed in cold acetone. The avidin-biotin immunoperoxidase and indirect immunofluorescence procedures were carried out as described (11, 13).

Immunochemical Procedures. Cultured cells were metabolically labeled with [$^{35}$S]methionine or [$^{3}$H]glucosamine, extracted in 0.01M Tris-HCI containing 0.5% Nonidet P-40, fractionated on ConA-Sepharose (Pharmacia), and used for immunoprecipitation experiments, followed by NaDodSO$_4$/polyacrylamide gel electrophoresis and fluorography, as described (4).

RESULTS

Figure 4:
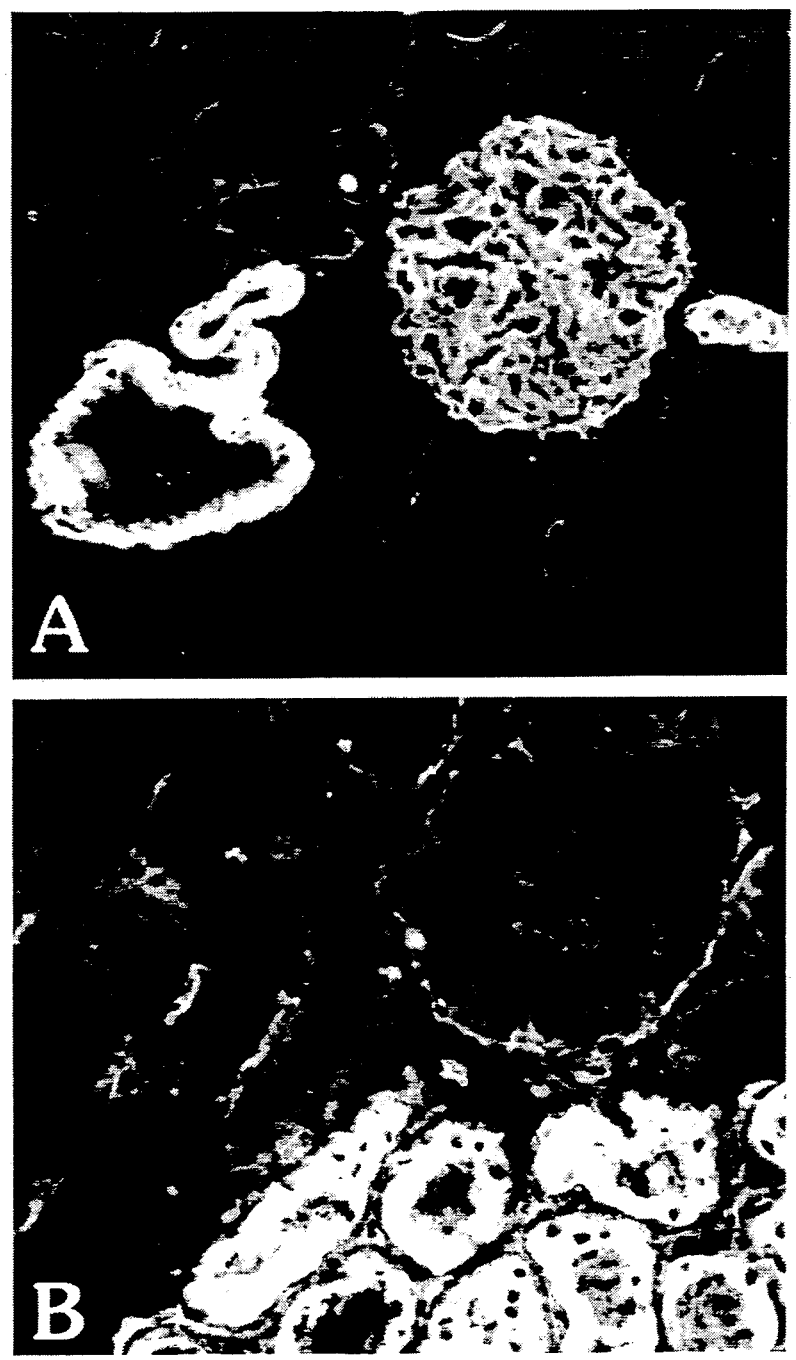
FIG. 4. Indirect immunoflourescence staining of normal adult kidney with mAb G253 (A) or anti-Thy-1 mAb K117 (B). Note G253 reactivity with glomerulus and vascular smooth muscle and Thy-1 reactivity restricted to convoluted portions of the renal tubules (upper left, glomerulus; lower left corner, straight portions of tubules). (Magnification, ×110.)
Figure 5:
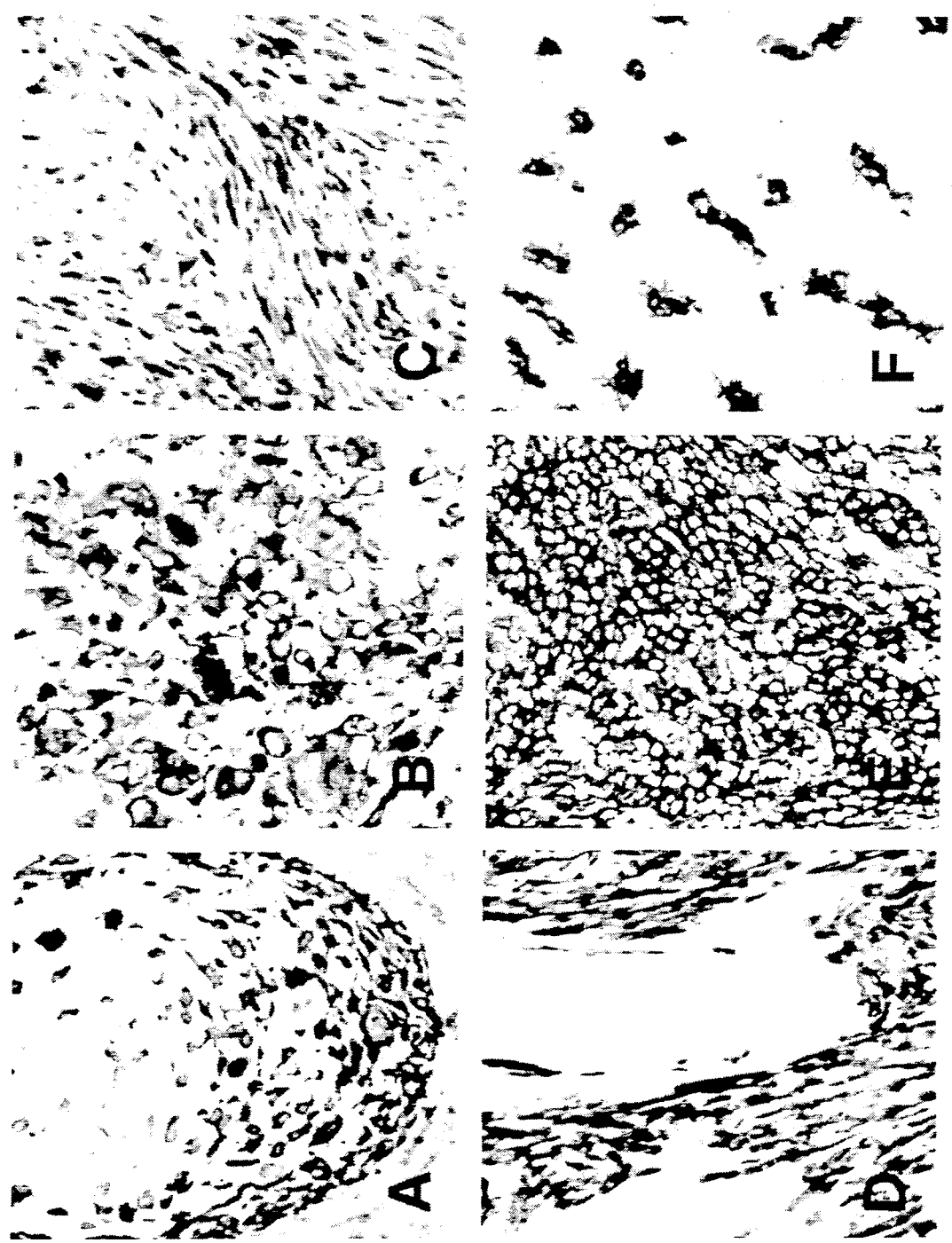
FIG. 5. Immunoperoxidase staining of tumor tissues with mAbs to cell surface antigens, mAb F19 tested with a chondrosarcoma (A), osteogenic sarcoma (B), fibrosarcoma (C), and colon cancer cells. Mesenchymal chondrosarcoma tested with mAb G171 (E) and parallel section tested with mAb K117 (anti-Thy-1) (F). Note Thy-1 expression in the perivascular connective tissue but not in the tumor cells, mAb K117 tested with a ganglioneuroblastoma (G) and malignant Schwannoma (H), (I) mAb G171 tested with a meningioma. Avidin-biotin immunoperoxidase staining of acetone-fixed frozen sections with hematoxylin counterstaining. (Magnification, ×140.)
Figure 5:
Figure 3:

Three types of antigenic maps were defined for the six monoclonal antibody-defined human cell-surface glycoproteins included in this invention. (i) For the cultured cell map, 12 established sarcoma cell lines and normal fibroblast cultures derived from 20 individuals were tested by the mixed hemadsorption rosetting assay (FIG. 1) and immunoprecipitation assays (FIG. 2) to define surface phenotypes of cultured mesenchymal cells. (ii) For the normal tissue map, a wide range of normal adult tissues (Table 1 and FIGS. 3 and 4) and several fetal tissues (skin, chest wall, kidney, colon, and lung; at 12-20 weeks of gestation) were tested by immunohistochemical procedures. (iii) For the tumor tissue map, tumor samples obtained from >200 patients with sarcomas or other malignancies (Table 2 and FIG. 5) were tested by immunohistochemistry. The following is a description of the most characteristic patterns of antigen expression in vitro and in vivo.

Figure 2:
FIG. 2. Immunoprecipitation analysis of human cell-surface antigens. ConA-bound fraction of [$^{35}$S]methionine-labeled 1ARC-EW1 cell extract tested with mAb G171 (lane A) or unrelated control mAb (lane B). [$^{3}$H]Glucosamine-label H$_s$ 74 fetal bone marrow fibroblasts tested with mAbs F19 (lane C), F24 (lane D), or G253 (lane E). [$^{3}$H]Glucosamine-labeled KD adult skin fibroblasts tested with mAbs F19 (lane E), F24 (lane G), or G253 (lane H). [$^{3}$H]Glucosamine-labeled SV40-transformed fibroblasts tested with mAb F19 (lane I), F24 (lane J), or G253 (lane K). [$^{3}$H]Glucosamine-labeled Hut 14 fibroblasts tested with mAb S5 (lane M) or control MAb (lane L). Immunopreciptitates were separated on NaDodSO$_4$/polyacrylamide gels under reducing conditions (extraction buffer containing dithiothreitol at 12 mg/ml). Molecular weights (M$_r$ 10$^{-3}$) of immunoprecipitated proteins are indicated on the right.
Figure 2:
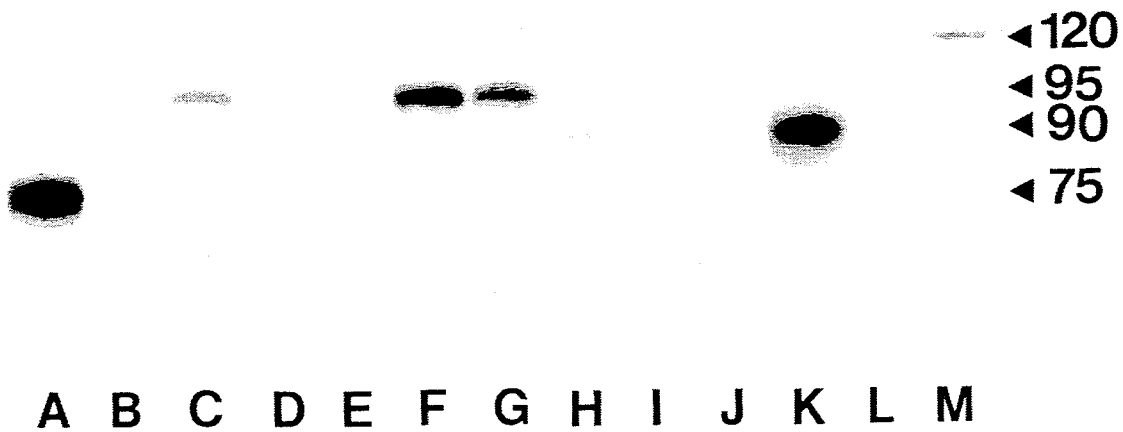

F19 Glycoprotein. Monoclonal antibody F19 defines $M_r$ 120,000 and 95,000 glycoproteins (gp120/95 or the F19 antigen) expressed on cultured fibroblasts and a proportion of sarcoma cell lines but not on simian virus 40 (SV40)-transformed fibroblasts (FIGS. 1 and 2). In normal adult tissues, F19 antigen was restricted to occasional fibroblasts and to a subset of pancreatic islet cells, presumably A cells (Table 1). F19 was more widely expressed in fetal mesenchymal tissues, including fibroblasts in the dermis (FIG. 3D), renal capsule, perichondrium and peritoneum. F19 was not found in the stromal fibroblasts of fetal kidney, colon, and lung or in fetal cartilage and skeletal muscle.

In a series of >200 malignant tumors tested by immunohistochemical procedures (Table 2), F19 antigen was found in most types of sarcomas tested, except for those with the "small round cell" phenotype (embryonal rhabdomyosarcoma, Ewing sarcoma, or mesenchymal chondrosarcoma). Neuroectodermal tumors, carcinomas, and lymphomas were consistently F19−, but strong induction of F19 was seen in the reactive stroma surrounding many of these F19 tumors (FIG. 5D). To determine whether other modes of mesenchymal activation also induce F19, were tested three skin samples with scar formation following surgical incisions. In each case, strong F19 expression was seen in the scar but not in adjacent normal dermis.

F24 Glycoprotein. Monoclonal antibody F24 defines a $M_r$ 95,000 glycoprotein (gp95 or the F24 antigen) expressed on cultured fibroblasts but not on most sarcoma cell lines or SV40-transformed fibroblasts (FIG. 1) gp95 comigrated on NaDodSO$_4$/polyacrylamide gels with the lower-molecular-weight band of the F19 glycoprotein (FIG. 2) and may be related to this molecule; however, the serological reactivities of monoclonal antibodies F24 and F19 differed significantly. Both monoclonal antibodies reacted equally with cultured fibroblasts (FIGS. 1 and 2), but monoclonal antibody F24 was unreactive with most F19+ sarcoma cell lines and did not show detectable reactivity with normal tissues or most tumors tested. Only a single, low-grade fibrosarcoma was found to show strong F24 immunostaining.

G171 Glycoprotein. Monoclonal antibody G171 defines a $M_r$ 75,000 glycoprotein (gp75 or the G171 antigen) expressed on a proportion of sarcoma cell lines and on lung fibroblasts (FIGS. 1 and 2); fibroblasts from other normal tissues (skin, kidney, colon, and bone) were consistently G171−, independent of the passage levels tested (range: primary culture to >15 passages). In normal adult tissues, G171 antigen was restricted to very few cell types (Table 1), including capillary endothelium and endocrine cells in the adrenal medulla. In the fetus, G171 was expressed in some additional mesenchymal tissues, such as skeletal muscle and cartilage. Fetal perichondrium and renal capsule are G171−, but fetal fibroblasts located at epithelial-mesenchymal junctions in skin (FIG. 3E), kidney, lung, and colon were G171+. Among the >200 tumors tested by immunohistochemical procedures, G171 was expressed in a large proportion of sarcomas and in meningiomas as well as subsets of Schwannomas, lung and ovarian cancers, and teratocarcinomas (Table 2). Other neuroectodermal tumors, carcinomas, and lymphomas were typed G171−. Similar to the F19 antigen, G171 was found in the reactive stroma surrounding many antigen-negative carcinomas and lymphomas and also in the F19+ dermal scars.

S5 Glycoprotein. Monoclonal antibody S5 defines a $M_r$ 120,000 glycoprotein (gp120 or the S5 antigen) expressed on cultured fibroblasts and sarcomas (FIGS. 1 and 2). Immunohistochemical analysis (Tables 1 and 2) showed that S5 antigen expression in vivo was much more restricted than was suggested by the wide distribution among cultured cells. In normal adult tissues, only visceral smooth muscle cells were strong S5 expressors (FIG. 3A); fibromuscular stroma of prostate and cervix showed weaker S5 immunoreactivity and vascular smooth muscle, cardiac, and skeletal muscle were S5− (FIG. 3B). In the fetus, both visceral smooth muscle and skeletal muscle were S5+ (FIG. 3C), but all other cell types tested were S5−. S5 expression in tumor tissues was restricted to a subset of leiomyosarcomas that generally showed weaker immunoreactivity than normal visceral smooth muscle.

G253 Glycoprotein. Monoclonal antibody G253 defines a $M_r$ 90,000 glycoprotein (gp90 or the G253 antigen) expressed on cultured sarcomas and SV40-transformed fibroblasts but not, or only weakly, on cultured normal fibroblasts (FIGS. 1 and 2). These results suggested that G253 antigen was a transformation-specific marker of mesenchymal cells, and we used immunohistochemical procedures to test 40 sarcomas for G253 expression. However, none of the tumor tissues showed antigen expression. In contrast, G253 was readily detected in normal vascular and visceral smooth muscle and in kidney glomeruli (FIG. 4A), demonstrating that lack of G253 reactivity with sarcoma tissues was not due to failure of the monoclonal antibody to detect antigen in acetone-fixed frozen tissue sections Thy-1. Monoclonal antibody K117 recognizes human Thy-1 (10), a $M_r$ 25,000 glycoprotein (gp25) expressed on cultured fibroblasts and sarcomas (FIG. 1). Immunohistochemical analysis showed Thy-1 expression in a variety of cell types (Table 1), including fibroblasts, muscularis mucosae of the gastrointestinal tract, fibromuscular stroma of prostate and cervix, connective tissue fibers (but not lymphoid cells) in spleen and lymph nodes (FIG. 3F), and specific portions of the renal tubules (FIG. 4B). In contrast, the muscularis propria of stomach and colon, smooth muscle of bladder and corpus uteri, smooth muscle of arterial blood vessels, skeletal and cardiac muscle were Thy-1− in the adult. Thy-1 expression in the fetus paralleled the adult pattern with two exceptions: basal keratinocytes of the skin and renal glomeruli expressed Thy-1 in the fetus but were Thy-1− in the adult. Contrary to previous suggestions (14), we did not find any Thy-1 expression in fetal skeletal muscle. Thy-1 expression in tumor tissues (Table 2) mirrored its distribution in normal tissues: most sarcomas and neuroectodermal tumors (FIGS. 5G and 5H) were Thy-1+, whereas most carcinomas were Thy-1−. Notable exceptions were the presence of Thy-1 in a proportion of ovarian carcinomas, the absence of Thy-1 from melanomas [consistent with the Thy-1− phenotype of most cultured melanoma cell lines (9)], and the lack of Thy-1 expression in Ewing sarcomas, embryonal rhabdomyosarcomas, and mesenchymal chondrosarcomas (FIG. 5F), a group of tumors distinguished by their "small round cell" phenotype.

DISCUSSION

Mesenchymal tissues comprise a range of cell types that differ in ebryological derivation, morphology, and function. At present, little is known about the surface antigen phenotypes of normal or neoplastic mesenchymal cells. In this invention, distinct patterns of expression for six cell-surface glycoproteins are defined that distinguish (i) normal mesenchymal cells of various lineages, (ii) mesenchymal cells at distinct states of development or differentiation, and (iii) subsets of mesenchymal tumors.

The F19 antigen is expressed in several fetal mesenchymal tissues, many sarcomas, the stroma of F19− carcinomas, scar tissue, and cultured fibroblasts, but is not generally found in normal adult mesenchyme. This pattern suggests that F19 is a cell-surface marker for proliferating mesenchymal cells and that its expression may be induced by normal growth factors or during malignant transformation. Since F19 expression is apparently down-regulated in SV40-transformed cultured fibroblasts, this mode of in vitro transformation and spontaneous transformation in vivo differ in their effects on surface antigen phenotype. Expression of the F24 antigen is similar in some respects to that of F19, but F24 is more restricted in its distribution and the two antigens differ biochemically.

The G171 antigen differs from F19 and F24 in molecular size and tissue distribution. For example, among cultured fibroblasts, G171 is expressed on only those derived from lung, whereas F19 and F24 are expressed on fibroblasts derived from several organs. Since none of these antigens is generally expressed in normal adult mesenchyme, it seems likely that their expression in the cultured cells is a response to mesenchymal growth or differentiation signals provided by the in vitro culture system and that fibroblasts derived from various organs respond differently to these extrinsic signals. Similarly, differential regulation for G171 and F19 by extrinsic signals in vivo and in vitro could account for other discordancies between the cultured cell maps and tissue maps of these antigens. For example, cultured Ewing sarcoma cells strongly express G171 and subsets of cultured astrocytomas and melanomas strongly express F19 (7), but the corresponding fresh tumor tissues are antigen-negative. Furthermore, cultured cells derived from fibrosarcomas are G171-, whereas the corresponding tumor tissues are generally G171+. Parallel analysis of tumor specimens and derived cell lines will help determine at which stage changes in antigenic phenotype occur.

The G253 and S5 antigens also exhibit various patterns of expression in tissues and in cultured cell panels. G253 appears to be a marker of transformed mesenchymal cells in vitro. It is strongly expressed in most sarcoma cell lines and in SV40-transformed fibroblasts but was not found in any uncultured sarcomas tested by immunohistochemical methods. S5 is expressed on a wide range of cultured mesenchymal and neuroectodermal cells, as well as on some cultured epithelial and hematopoietic cells (7), but in normal adult tissues the antigen is restricted to visceral smooth muscle. Moreover, among tumors tested by immunohistochemical methods, S5 is restricted to leiomyosarcomas. Analysis of normal fetal tissues reveals that additional cell types express S5 transiently during development (e.g., skeletal muscle). It is thus conceivable that the wide distribution of S5 and G253 on cultured cells reflects specific activation of early developmental traits in the cultures or adaptive changes induced by altered cell-substrate or cell/cell interactions in cells grown on plastic culture surfaces. Since uncultured sarcomas and reactive mesenchyme do not generally express G253 or S5, it is less likely that they are linked to proliferation, as was suggested for F19.

The Thy-1 antigen was first identified as a thymocyte differentiation antigen in mice but has subsequently been found in lymphoid and neural tissues of several species, including humans (15). The present invention provides an extensive analysis of Thy-1 expression in human tumors and normal tissues. With respect to mesenchymal tissues, it was found that subsets of normal cells can be distinguished by their Thy-1 phenotypes (e.g., visceral and vascular smooth muscle in various sites differ in antigen expression) and that sarcomas are generally Thy-1+, except for those with "small round cell" phenotype (Ewing sarcoma, embryonal rhabdomyosarcoma, and mesenchymal chondrosarcoma).

Detailed analysis (cultured cell map, normal tissue map, and tumor tissue map) of six distinct human cell surface glycoproteins has revealed characteristic patterns of antigen expression in normal developing and adult mesenchyme and in mesenchymal tumors. It is apparent that typing with monoclonal antibodies F19, G171, S5, and 117 identifies subsets of sarcomas with distinctive antigenic phenotypes, and it is possible that these antigenic patterns correlate with differences in histogenesis or biological behavior. It has been shown (16) that differential expression of the cell surface receptor for nerve growth factor also distinguishes subsets of human sarcomas, but in contrast to the glycoproteins described here, the receptor for nerve growth factor is selectively expressed in Ewing sarcomas and embryonal rhabdomyosarcomas. Since expression of F19, G171, and S5 is highly restricted in normal tissues, they may be useful targets for immunolocalization or immunotherapy of antigen-expressing tumors.

TABLE 1

DISTRIBUTION OF MONOCLONAL ANTIBODY-DEFINED HUMAN CELL SURFACE ANTIGENS IN NORMAL ADULT TISSUES

| Antigen | Antigen-expressing cell types |
| --- | --- |
| F19 | Occasional fibroblast; pancreatic islet A cells |
| G171 | Capillary endothelium; adrenal medullary cells; myoepithelial cells; pneumocytes (weak) |
| S5 | Visceral smooth muscle; vascular endothelium (weak) |
| Thy-1 | CNS white and gray matter; peripheral nerves; PNS ganglion and glial cells; myoepithelial cells; mammary ducts; renal tubules (pars convoluta), adrenal endocrine cells; visceral smooth muscle; vascular endothelium; fibroblasts |

Acetone-fixed frozen sections were tested by the avidin-biotin immunoperoxidase procedure. Tissues included were brain, spinal cord, autonomic ganglia, peripheral nerves, skin, mammary gland, parotid gland, tongue, esophagus, stomach, colon, liver, pancreas, bronchus, lung, kidney, urinary bladder, testis, ovary, prostate, uterus, lymph node, spleen, thymus, adrenal gland, thyroid gland, and skeletal and cardiac muscle.

TABLE 2

DISTRIBUTION OF MONOCLONAL ANTIBODY-DEFINED HUMAN CELL SURFACE ANTIGENS IN TUMOR TISSUES

| Tumor type | Antigen expression (antigen-positive/total tested) | | | |
| --- | --- | --- | --- | --- |
| | F19 | G171 | S5 | Thy-1 |
| Sarcomas | | | | |
| Fibrosarcoma | 5/5 | 4/5 | 0/5 | 5/5 |
| Malignant fibrous histiocytoma | 4/4 | 4/4 | 0/4 | 3/4 |
| Leiomyosarcoma | 8/10 | 3/10 | 6/10 | 7/10 |
| Osteosarcoma | 2/4 | 4/4 | 0/4 | 3/4 |
| Chondrosarcoma | 2/2 | 2/2 | 0/2 | 2/2 |
| Liposarcoma | 3/4 | 3/4 | 0/4 | 3/4 |
| Synovial sarcoma | 1/6 | 5/6 | 0/6 | 6/6 |
| Embryonal rhabdomyosarcoma | 0/6 | 1/6 | 0/6 | 2/6 |
| Ewing sarcoma | 0/8 | 0/8 | 0/8 | 0/8 |
| Mesenchymal chondrosarcoma | 0/2 | 1/2 | 0/2 | 0/2 |
| Rhabdomyosarcoma | 0/2 | 1/1 | 0/1 | 2/2 |
| Undifferentiated | 2/3 | 2/3 | 0/2 | 3/3 |
| Neuroectodermal tumors | | | | |
| Melanoma | 0/12 | 0/12 | 0/12 | 1/12 |
| Astrocytoma | 0/12 | 0/12 | 0/12 | 12/12 |
| Schwannoma | 2/7 | 2/6 | 0/4 | 6/7 |
| Neuroblastoma | 0/5 | 0/5 | 0/5 | 5/5 |
| Meningioma | 0/5 | 5/5 | 0/5 | 5/5 |
| Carcinomas | | | | |
| Neuroendocrine | 0/7 | 0/7 | 0/7 | 4/7 |
| Colorectal | 0/18 | 0/18 | 0/18 | 0/18 |
| Gastric | 0/6 | 0/6 | 0/5 | 0/6 |
| Skin | 0/8 | 0/8 | 0/8 | 0/8 |
| Lung | 0/10 | 2/10 | 0/8 | 0/8 |
| Breast | 0/13 | 0/13 | 0/13 | 0/13 |

TABLE 2-continued
DISTRIBUTION OF MONOCLONAL ANTIBODY-DEFINED HUMAN CELL SURFACE ANTIGENS IN TUMOR TISSUES

| Tumor type | Antigen expression (antigen-postive/total tested) | | | |
|---|---|---|---|---|
| | F19 | G171 | S5 | Thy-1 |
| Ovarian | 0/21 | 7/21 | 0/21 | 7/20 |
| Testicular | 0/5 | 4/5 | 0/5 | 3/4 |
| Kidney | 0/9 | 0/9 | 0/9 | 0/9 |
| Bladder | 0/6 | 0/6 | 0/6 | 0/6 |
| Others | 0/10 | 0/10 | 0/10 | 0/10 |
| Lymphomas | | | | |
| Hodgkin | 0/5 | 0/4 | 0/4 | 5/5 |
| Non-Hodgkin | 0/12 | 0/12 | 0/11 | 8/14 |

Acetone-fixed frozen sections were tested by the avidin-biotin immunoperoxidase procedure. Numbers indicate the proportion of tumors obtained from different patients that express the respective antigens (number antigen-positive/total number tested). Strong intratumoral heterogeneity in antigen expression was only seen for G171 in the lung cancers listed as G171+.

References

1. Boyse, E. A. & Old, L. J. (1969) *Annu. Rev. Genet.* 3, 269-290.
2. Foon, K. A. & Todd, R. F. (1986) *Blood* 68, 1-31.
3. Houghton, A. N., Eisinger, M., Albino, A. P., Cairnocross, J. G. & Old, L. J. (1982) *J. Exp. Med.* 56, 1755-1766.
4. Rettig, W. J., Murty, V. V. V. S., Mattes, M. J., Chaganti, R.S. K. & Old, L. J. (1986) *J. Exp. Med.* 164, 581-1599.
5. Rettig, W. J., Garin Chesa, P., Jennings, M. T., Spengler, B. A., Melamed, M. R., Oettgen, H. F., Biedler, J. L. & Old, L. J. (1985) *Proc. Natl. Acad. Sci. USA* 82, 6894-6898.
6. Rettig, W. J., Spengler, B. A., Garin Chesa, P., Old, L. J. & Biedler, J. L (1987) *Cancer Res.* 47, 1383-1389.
7. Rettig, W. J., Garin Chesa, P., Beresford, H. R., Feickert, H. J., Jennings, M. T., Cohen, J., Oettgen, H. F. & Old, L. J. (1986) *Cancer Res.* 46, 6406-6412.
8. Rettig, W. J., Cordon-Cardo, C., Ng, J. S. C., Oettgen, H. F., Old, L. J. & Lloyd, K. 0. (1985) *Cancer Res.* 45, 815-821.
9. Rettig, W. J. Dracopoli, N. C., Garin Chesa, P., Spengler, B A., Beresford, H. R., Davies, P., Biedler, J. L. & Old, L. J. (1985) *J. Exp. Med.* 162, 1603-1619.
10. Rettig, W. J., Nishimura, H., Yenamandra, A. K., Seki, T., Obata, F., Beresford, H. R., Old, L. J. & Silver, J. (1987) *J. Immunol.*, 138, 4484-4489.
11. Gordon, J., Garin Chesa, P., Nishimura, H., Rettig, W. J., Maccari, J. E., Endo, T., Seravalli, E., Seki, T. & Silver, J. (1987) *Cell* 50, 445-452.
12. Sato, Y., Mukai, K., Watanabe, S., Goto, M. & Shimosato, Y. (1986) *Am. J. Pathol.* 125, 431-435.
13. Garin Chesa, P., Rettig, W. J. & Melamed, M. R. 14. Walsh, F. & Ritter, M. A. (1981) *Nature (London)* 289, 60-64.
15. Williams, A. F. & Gagnon, J. (1982) *Science* 216, 696-703.
16. Garin Chesa, P., Rettig, W. J., Thomson, T. M., Old, L. J. & Melamed, M. R., *J. Histochem. Cytochem.*, in press.

What is claimed is:

1. A method of identifying noncultured mesenchymal tissues as normal, proliferatively active or malignant which comprises contacting a noncultured mesenchymal tissue sample with at least one monoclonal antibody selected from the group consisting of monoclonal antibodies F19, F24, G171, S5, G253 and K117 (produced by the hybridoma cell lines ATCC Nos. HB 8269, HB9257, HB 9254, HB 9255, HB 9207, and HB 8553, respectively) under suitable conditions so as to form a complex between the sample and the selected antibody or antibodies, detecting the presence or absence of any complex so formed and identifying the noncultured mesenchymal tissue as normal when the following reactions are observed:

| Antibody | Positive Antibody Response |
|---|---|
| F19 | Occasional fibroblast; pancreatic islet A cells |
| G171 | Capillary endothelium; adrenal medullary cells; myoepithelial cells; pneumocytes (weak) |
| S5 | visceral smooth muscle; vascular endothelium (weak) |
| K117 | CNS white and gray matter; peripheral nerves; PNS ganglion and glial cells; myoepithelial cells; mammary ducts; renal tubules (pars convoluta); adrenal endocrine cells; visceral smooth muscle; vascular endothelium; fibroblasts | and identifying the noncultured mesenchymal tissues as malignant by comparing the presence of absence of a positive reaction to the following:

| | MALIGNANT | | | |
|---|---|---|---|---|
| | Antibody | | | |
| Tumor type | F19 | G171 | S5 | K117 |
| Sarcomas | | | | |
| Fibrosarcoma | + | + | − | + |
| Malignant fibrous histiocytoma | + | + | − | + |
| Leiomyosarcoma | + | − | + | + |
| Osteosarcoma | + | + | − | + |
| Chondrosarcoma | + | + | − | + |
| Liposarcoma | + | + | − | + |
| Synovial sarcoma | − | + | − | + |
| Embryonal rhabdomyosarcoma | − | − | − | − |
| Ewing sarcoma | − | − | − | − |
| Mesenchymal chondrosarcoma | − | + | − | − |
| Rhabdomyosarcoma | − | + | − | + |
| Undifferentiated | + | + | − | + |
| Neuroectodermal tumors | | | | |
| Melanoma | − | − | − | − |
| Astrocytoma | − | − | − | + |
| Schwannoma | − | − | − | + |
| Neuroblastoma | − | − | − | + |
| Meningioma | − | + | − | + |
| Carcinomas | | | | |
| Neuroendocrine | − | − | − | + |
| Colorectal | − | − | − | − |
| Gastric | − | − | − | − |
| Skin | − | − | − | − |
| Lung | − | − | − | − |
| Breast | − | − | − | − |
| Ovarian | − | − | − | − |
| Testicular | − | + | − | + |
| Kidney | − | − | − | − |
| Bladder | − | − | − | − |
| Others | − | − | − | − |
| Lymphomas | | | | |
| Hodgkin | − | − | − | + |
| Non-Hodgkin | − | − | − | + | and identifying the noncultured mesenchymal tissue as proliferatively active when the following reactions are observed:

|  | Antibody | | | |
| --- | --- | --- | --- | --- |
|  | F19 | F24 | S5 | G253 |
| Positive Antigen Expression | + | + | − | − | thereby identifying non-cultured mesenchymal tissues as normal, proliferatively active or malignant.

2. The method of claim 1 wherein the noncultured mesenchymal tissue sample is human adult tissue.

3. The method of claim 1 wherein the noncultured mesenchymal tissue sample is human fetal tissue.

4. A method of distinguishing subsets of noncultured sarcomas with distinctive antigenic phenotypes which comprises contacting a noncultured sarcoma tissue sample with at least one monoclonal antibody selected from the group consisting of monoclonal antibodies F19, G171, S5 and K117 (produced by hybridoma cell lines ATCC Nos. HB 8269, HB 9254, HB 9255, and HB 8553, respectively) under suitable conditions so as to form a complex between the sample and the selected antibody or antibodies, detecting the presence of any complex so formed, and comparing the presence or absence of any complex with the following:

| Tumor type | Antibody | | | |
| --- | --- | --- | --- | --- |
|  | F19 | G171 | S5 | K117 |
| Sarcomas | | | | |
| Fibrosarcoma | + | + | − | + |
| Malignant fibrous histiocytoma | + | + | − | + |
| Leiomyosarcoma | + | − | + | + |
| Osteosarcoma | + | + | − | + |
| Chondrosarcoma | + | + | − | + |
| Liposarcoma | + | + | − | + |
| Synovial sarcoma | − | + | − | + |
| Embryonal rhabdomyosarcoma | − | − | − | − |
| Ewing sarcoma | − | − | − | − |
| Mesenchymal chondrosarcoma | − | + | − | − |
| Rhabdomyosarcoma | − | + | − | + |
| Undifferentiated | + | + | − | + | thereby distinguishing subsets of noncultured sarcomas with distinctive antigenic phenotypes.

5. A method of diagnosing noncultured mesenchymal tumors which comprises contacting a noncultured mesenchymal tissue sample with at least one monoclonal antibody selected from the group consisting of monoclonal antibodies F19, G171, K117 and S5 (produced by the hybridoma cell lines ATCC Nos. HB 8269, HB 9254, HB 8553 and HB 9255, respectively) under suitable conditions so as to form a complex between the sample and the selected antibodies or antibody, detecting the presence or absence of any complex, and comparing the presence or absence of any complex with the following:

| Tumor type | Antibody | | | |
| --- | --- | --- | --- | --- |
|  | F19 | G171 | S5 | K117 |
| Sarcomas | | | | |
| Fibrosarcoma | + | + | − | + |
| Malignant fibrous histiocytoma | + | + | − | + |
| Leiomyosarcoma | + | − | + | + |
| Osteosarcoma | + | + | − | + |
| Chondrosarcoma | + | + | − | + |
| Liposarcoma | + | + | − | + |
| Synovial sarcoma | − | + | − | + |
| Embryonal rhabdomyosarcoma | − | − | − | − |
| Ewing sarcoma | − | − | − | − |
| Mesenchymal chondrosarcoma | − | + | − | − |
| Rhabdomyosarcoma | − | + | − | + |
| Undifferentiated | + | + | − | + |
| Neuroectodermal tumors | | | | |
| Melanoma | − | − | − | − |
| Astrocytoma | − | − | − | + |
| Schwannoma | − | − | − | + |
| Neuroblastoma | − | − | − | + |
| Meningioma | − | + | − | + |
| Carcinomas | | | | |
| Neuroendocrine | − | − | − | + |
| Colorectal | − | − | − | − |
| Gastric | − | − | − | − |
| Skin | − | − | − | − |
| Lung | − | − | − | − |
| Breast | − | − | − | − |
| Ovarian | − | − | − | − |
| Testicular | − | + | − | + |
| Kidney | − | − | − | − |
| Bladder | − | − | − | − |
| Others | − | − | − | − |
| Lymphomas | | | | |
| Hodgkin | − | − | − | + |
| Non-Hodgkin | − | − | − | + | thereby diagnosing noncultured mesenchymal tumors.

6. A hybridomal cell line (ATCC No. HB9254).

7. The monoclonal antibody G171 produced by the hybridoma cell line (ATCC No. HB9254) of claim 6.

* * * * *

UNITED STATES PATENT AND TRADEMARK OFFICE
CERTIFICATE OF CORRECTION

PATENT NO. : 5,059,523

DATED : October 22, 1991

INVENTOR(S) : Wolfgang J. Rettig, et al.

Page 1 of 3

It is certified that error appears in the above-identified patent and that said Letters Patent is hereby corrected as shown below:

In column 1, line 46; "mesechymal" should read —mesenchymal—.

In column 2, line 11; "ascities" should read —ascites—.

In column 2, line 43; "Immunopreciptitates" should read —Immunoprecipitates—

In column 2, line 48; "Immunopreroxidase" should read —Immunoperoxidase—.

In column 2, line 53; "epithelialmescenchymal" should read —epithelial-mesenchymal—.

In column 2, lines 59-60; "AMeX/paraffine-embedded" should read —AMeX/paraffin-embedded—.

In column 3, line 38; "mesechymal" should read —mesenchymal—.

In column 5, line 5; "were tested three skin samples" should read —three skin samples were tested—.

In Col. 6, line 47, "ebryological" should read —embryological—.

In claim 1, column 10, line 2; "HB 9207" should read —HB 9706—.

UNITED STATES PATENT AND TRADEMARK OFFICE
CERTIFICATE OF CORRECTION

PATENT NO. : 5,059,523
DATED : October 22, 1991
INVENTOR(S) : Wolfgang J. Rettig Page 2 of 3

Figure 3:
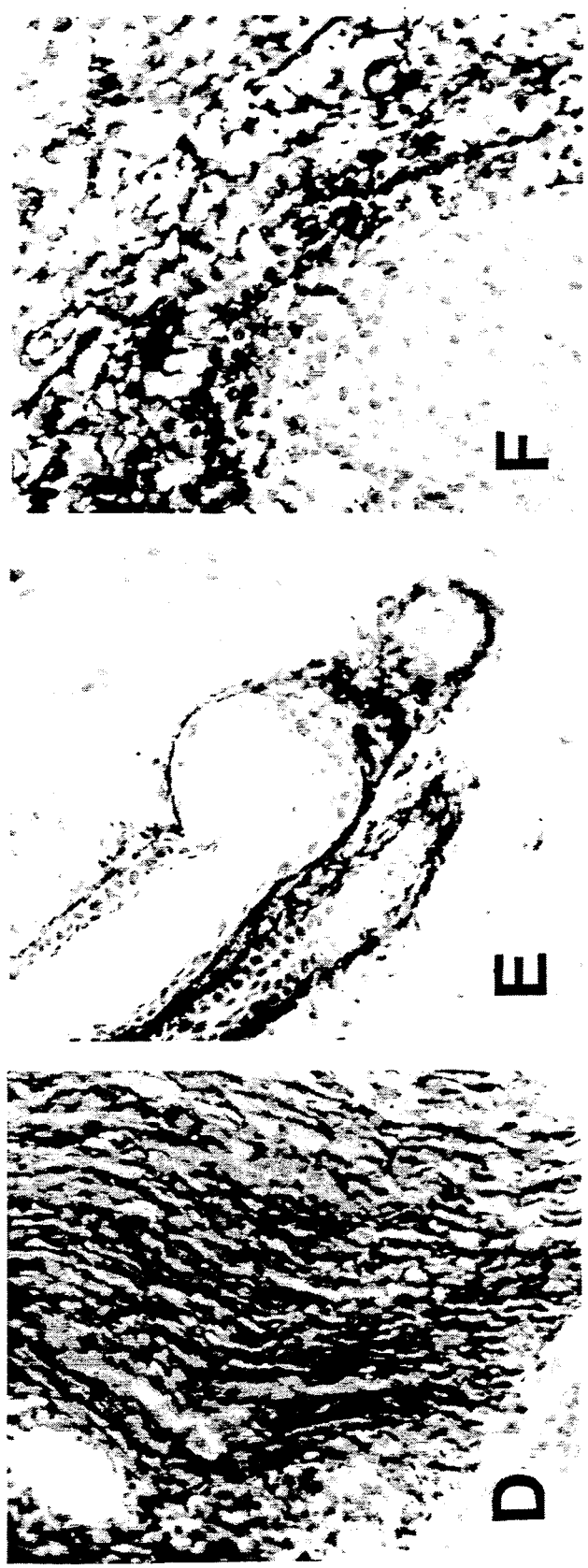
FIG. 3. Immunopreroxidase staining of normal human tissues with mAbs to cell surface antigens, mAb S5 tested with smooth muscle of adult urinary bladder (A), adult skeletal muscle (B), and fetal skeletal muscle (C), (D) mAb F19 tested with fetal dermis. Note reactivity with fibroblasts but not epithelialmesenchymal junction of the hair follicle, (F) mAb K117 (anti-Thy-1) tested with adult spleen. Note reactivity with connective tissue fibers but not lymphoid cells (germinal center shown in top left corner). Avidin-biotin immunoperoxidase procedure with hematoxylin counterstaining, (A-E) Acetone-fixed frozen tissues, (E) AMeX/paraffine-embedded tissue (12), (Magnification, for A×220 or for B-F×140.)

It is certified that error appears in the above-indentified patent and that said Letters Patent is hereby corrected as shown below:

Figure 2 on sheet 6 of 10 should be deleted to be replaced with Figure 3, panels A,B and C as shown on the attached sheet.

Signed and Sealed this

Third Day of May, 1994

*Attest:*

BRUCE LEHMAN

*Attesting Officer*     Commissioner of Patents and Trademarks